US012688594B2

(12) United States Patent
Kolen et al.

(10) Patent No.: US 12,688,594 B2
(45) Date of Patent: Jul. 21, 2026

(54) METHOD OF REGISTERING ULTRASOUND IMAGES TO AN ANATOMICAL MAP

(71) Applicant: KONINKLIJKE PHILIPS N.V., Eindhoven (NL)

(72) Inventors: Alexander Franciscus Kolen, Eindhoven (NL); Martinus Bernardus Van Der Mark, Best (NL); Gerardus Henricus Maria Gijsbers, Liempde (NL); Godefridus Antonius Harks, Rijen (NL)

(73) Assignee: Koninklijke Philips N.V., Eindhoven (NL)

( * ) Notice: Subject to any disclaimer, the term of this patent is extended or adjusted under 35 U.S.C. 154(b) by 530 days.

(21) Appl. No.: 18/025,060

(22) PCT Filed: Sep. 7, 2021

(86) PCT No.: PCT/EP2021/074531
§ 371 (c)(1),
(2) Date: Mar. 7, 2023

(87) PCT Pub. No.: WO2022/053440
PCT Pub. Date: Mar. 17, 2022

(65) Prior Publication Data
US 2023/0334679 A1     Oct. 19, 2023

(30) Foreign Application Priority Data
Sep. 10, 2020     (EP) ..................................... 20195407

(51) Int. Cl.
A61B 8/00        (2006.01)
A61B 5/0538      (2021.01)
(Continued)

(52) U.S. Cl.
CPC ............ G06T 7/344 (2017.01); A61B 5/0538 (2013.01); A61B 5/061 (2013.01); A61B 8/5261 (2013.01)

(58) Field of Classification Search
CPC ....... G06T 7/344; A61B 5/0538; A61B 5/061; A61B 8/4245; A61B 8/4254; A61B 8/5261; A61B 5/367; A61B 34/20; G01B 7/004
See application file for complete search history.

(56) References Cited

U.S. PATENT DOCUMENTS

| | | | |
|---|---|---|---|
| 6,690,963 | B2 | 2/2004 | Ben-Haim |
| 10,004,459 | B2 | 6/2018 | Werneth |

(Continued)

FOREIGN PATENT DOCUMENTS

| | | |
|---|---|---|
| EP | 1852824 A1 | 11/2007 |
| EP | 2208466 A1 | 7/2010 |
| WO | 2018130974 A1 | 7/2018 |

OTHER PUBLICATIONS

International Search Report and Written Opinion of PCT/EP2021/074531, dated Nov. 11, 2021.

*Primary Examiner* — Kent Yip

(57) ABSTRACT

A mechanism for registering ultrasound images with an anatomical map generated using a dielectric imaging process. The positions of electrodes that move with the ultrasound probe are monitored using the same dielectric imaging system that generated the anatomical map. The position at which ultrasound images are generated is captured, and this information is used to register the ultrasound image(s) with respect to the anatomical map.

15 Claims, 4 Drawing Sheets

(51) Int. Cl.
  *A61B 5/06*      (2006.01)
  *G06T 7/33*      (2017.01)

(56)        References Cited

U.S. PATENT DOCUMENTS

|  |  |  |  |
|---|---|---|---|
| 11,250,601 B2 * | 2/2022 | Chen | ..................... G06N 3/045 |
| 2006/0178587 A1 | 8/2006 | Khoury | |
| 2007/0049817 A1 | 3/2007 | Preiss | |
| 2011/0034806 A1 * | 2/2011 | Hartov | ................. A61B 8/4411 |
|  |  |  | 600/443 |
| 2016/0228200 A1 | 8/2016 | Denissen | |
| 2019/0099211 A1 | 4/2019 | Altmann | |
| 2019/0313910 A1 | 10/2019 | Vignon et al. | |
| 2019/0343401 A1 | 11/2019 | Scharf | |

\* cited by examiner

METHOD OF REGISTERING ULTRASOUND IMAGES TO AN ANATOMICAL MAP

CROSS-REFERENCE TO PRIOR APPLICATIONS

This application is the U.S. National Phase application under 35 U.S.C. § 371 of International Application No. PCT/EP2021/074531, filed on Sep. 7, 2021, which claims the benefit of European Patent Application No. 20195407.0, filed on Sep. 10, 2020. These applications are hereby incorporated by reference herein.

FIELD OF THE INVENTION

The present invention relates to the field of medical imaging, and in particular to the field of registering different imaging modalities together.

BACKGROUND OF THE INVENTION

There is an ongoing interest in improving a clinician's understanding of a volume of interest of a patient, e.g. of a patient's heart, to aid in treatment of the patient. Various imaging techniques have been proposed to generate (2D or 3D) images or reconstructions of a volume of interest, such as MRI, CT and ultrasound imaging techniques.

A recent development in medical imaging has been dielectric imaging. A dielectric imaging process involves monitoring electric field(s) generated between electrodes of a catheter inserted into a volume of interest within a patient and those of electrical fields generated between electrodes positioned externally to the patient and monitored by the catheter electrodes to derive dielectric properties of tissue directly surrounding the catheter. The information obtained is then used to construct an anatomical map of the volume of interest. One example approach for constructing an anatomical map from such information is described by WO 2018/130974 A1, although other examples would be apparent to the skilled person.

However, whilst dielectric imaging provides useful information about the structure of a volume of interest, it is difficult to obtain information behind the wall of the volume of interest and there is also a desire to ensure that real time and/or high-resolution information on features within and behind the volume of interest can be identified by a clinician.

There is therefore a desire to provide a mechanism by which additional "real-time" information of a patient can be obtained and provided alongside the anatomical map of the volume of interest.

SUMMARY OF THE INVENTION

The invention is defined by the claims.

According to examples in accordance with an aspect of the invention, there is provided an imaging system for registering at least one ultrasound image obtained using an ultrasound probe during an ultrasound imaging process to an anatomical map obtained using a dielectric imaging process.

The imaging system comprises: a dielectric imaging system configured to generate an anatomical map of a volume of interest of a subject using a dielectric imaging process; an ultrasound imaging system configured to generate one or more ultrasound images of the volume of interest, the ultrasound imaging system comprising: an ultrasound probe, preferably an intracardiac echographic catheter probe, configured to obtain ultrasound data of the volume of interest during an ultrasound imaging process; an ultrasound processing module configured to process the ultrasound data, obtained during the ultrasound imaging process, to generate at least one ultrasound image of the volume of interest; and two or more electrodes, connectable to the dielectric imaging system, and configured to move together with a movement of the ultrasound probe, wherein the dielectric imaging system is further configured to connect to the two or more electrodes of the ultrasound imaging system and monitor positions of the two or more electrodes, and thereby the ultrasound probe, during the ultrasound imaging process; and a registration module configured to register a position of each at least one ultrasound image with respect to the anatomical map of the volume of interest using the monitored positions of the ultrasound probe.

The ultrasound probe is a probe designed for internal ultrasound imaging, and called be labelled an "internal ultrasound probe". Examples include an intravascular ultrasound probe (i.e. a probe designed for passage through one or more blood vessels), an endoscopic ultrasound probe, a transrectal ultrasound probe or the like. In some examples, the ultrasound probe is an intracardiac echographic catheter probe.

The present disclosure proposes a mechanism for tracking the position of an ultrasound probe within a volume of interest using a dielectric imaging system. This is achieved by configuring an ultrasound imaging system to comprise two or more electrodes that move with the ultrasound probe. The dielectric imaging system controls and/or monitors the two or more electrodes, to thereby determine a relative position of the two or more electrodes within the volume of interest.

The proposed approach enables the position of ultrasound images to be registered with respect to an anatomical map generated by the dielectric imaging system. In particular, as the same system is used to generate the anatomical map and to track the ultrasound probe, the position of ultrasound images with respect to the anatomical map can be readily derived.

The mechanism enables real-time and high-quality ultrasound images to be presented alongside the anatomical map, to improve a user's understanding of the volume of interest. In particular, the mechanism provides an approach for registering a location of an ultrasound image with respect to an anatomical structure, to provide context for the ultrasound image.

The dielectric imaging system may be configured to monitor positions of the two or more electrodes by monitoring an electrical response of each electrode to one or more electric fields induced in the subject. The present disclosure recognizes that the location of an electrode within the volume of interest can be monitored by monitoring an electrical response (e.g. voltage response) of that electrode with respect to an electric field that has been induced in the volume of interest (e.g. by electrodes external to the subject).

In some examples, the ultrasound imaging system, the dielectric imaging system and/or the registration module is configured to determine an imaging direction of each at least one ultrasound image; and the registration module is configured to register an orientation of each at least one ultrasound image with respect to the anatomical map of the volume of interest based on the determined imaging direction of each at least one ultrasound image.

The ultrasound imaging probe may further comprise an accelerometer configured to monitor an orientation of the ultrasound probe, with respect to the volume of interest, during the ultrasound imaging process; and the imaging system may be configured to determine an imaging direction of each at least one ultrasound image based on the monitored orientation of the ultrasound probe during the ultrasound imaging process.

Optionally, the registration module is configured to perform, for at least one ultrasound image, an image feature matching process on the ultrasound image and the anatomical map to thereby identify an imaging direction of each at least one ultrasound image with respect to the anatomical map.

The registration module may be configured to receive a user input indicating, for at least one ultrasound image, an orientation of the at least one ultrasound image with respect to the anatomical map.

The two or more electrodes of the ultrasound imaging system may comprise two or more non-cylindrical electrodes positioned along a longitudinal axis of the ultrasound probe. The dielectric imaging system may be configured to determine an orientation of the two or more electrodes, and therefore the ultrasound probe, by monitoring electric fields and therefore the 3D positions by the non-cylindrical electrodes.

Optionally, at least one of the electrodes of the ultrasound system is used as a support structure for one or more elements of the ultrasound probe. In particular, pre-existing metal supports for elements of the ultrasound probe could be repurposed for use as an electrode for monitoring the position of the ultrasound probe (and thereby the position of the ultrasound images) with respect to the anatomical map.

In some examples, the ultrasound system further comprises an optical fiber that moves together with a movement of the ultrasound probe, and the imaging system is adapted to further comprise an optical shape determination module configured to transmit and receive electromagnetic radiation along the optical fiber of the ultrasound system to monitor a shape of the optical fiber, and thereby a position and/or orientation of the optical fiber and the ultrasound probe.

Optionally, the imaging system further comprises a three-dimensional medical image obtainer, configured to obtain a three-dimensional medical image of the patient, containing at least the volume of interest; and the registration module is configured to use the monitored shape of the optical fiber to further register the position of the at least one ultrasound image, and optionally the anatomical map, with respect to the three-dimensional medical image. The three-dimensional medical image may, for example, be a computed tomography (CT) image.

The at least two electrodes may be disposed in or on a sheath that houses the ultrasound probe. In other examples, they are disposed on the ultrasound probe itself.

The dielectric imaging system may be configured to generate the anatomical map of the volume of interest by performing a dielectric imaging process using the two or more electrodes of the ultrasound imaging probe.

The imaging system may further comprise a display configured to display: the anatomical map generated by the dielectric imaging system; and one or more ultrasound images obtained by the ultrasound imaging system, wherein the one or more ultrasound images overlay the anatomical map based on at least the registered position of each one or more ultrasound image with respect to the anatomical map.

There is also proposed a computer-implemented method for registering at least one ultrasound image obtained using an ultrasound probe during an ultrasound imaging process to an anatomical map.

The computer-implemented method comprises: obtaining an anatomical map of a volume of a subject generated using a dielectric imaging system configured to use dielectric imaging to obtain an anatomical map; monitoring, during the ultrasound imaging process, positions of the ultrasound probe with respect to the subject using the dielectric imaging system, wherein the ultrasound probe comprises two or more electrodes detectable by the dielectric imaging system; and using the monitored positions of the ultrasound probe to register at least one ultrasound image generated using the ultrasound probe with a respective position in the anatomical map, to thereby register at least one ultrasound image to the anatomical map.

There is also proposed a computer program product comprising instructions which, when executed by a suitable computer or processing system, cause the computer to carry out the method herein described.

The present disclosure also proposes a computer program (product) comprising instructions which, when the program is executed by a computer or processing system, cause the computer or processing system to carry out (the steps of) any herein described method. The computer program (product) may be stored on a non-transitory computer readable medium.

Similarly, there is also proposed a computer-readable (storage) medium comprising instructions which, when executed by a computer or processing system, cause the computer or processing system to carry out (the steps of) any herein described method. There is also proposed computer-readable data carrier having stored thereon the computer program (product) previously described. There is also proposed a data carrier signal carrying the computer program (product) previously described.

The skilled person would be readily capable of adapting any herein described method to reflect embodiments of herein described apparatus, systems and/or processors, and vice versa. A similar understanding would be made by the skilled person with respect to a computer program (product).

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
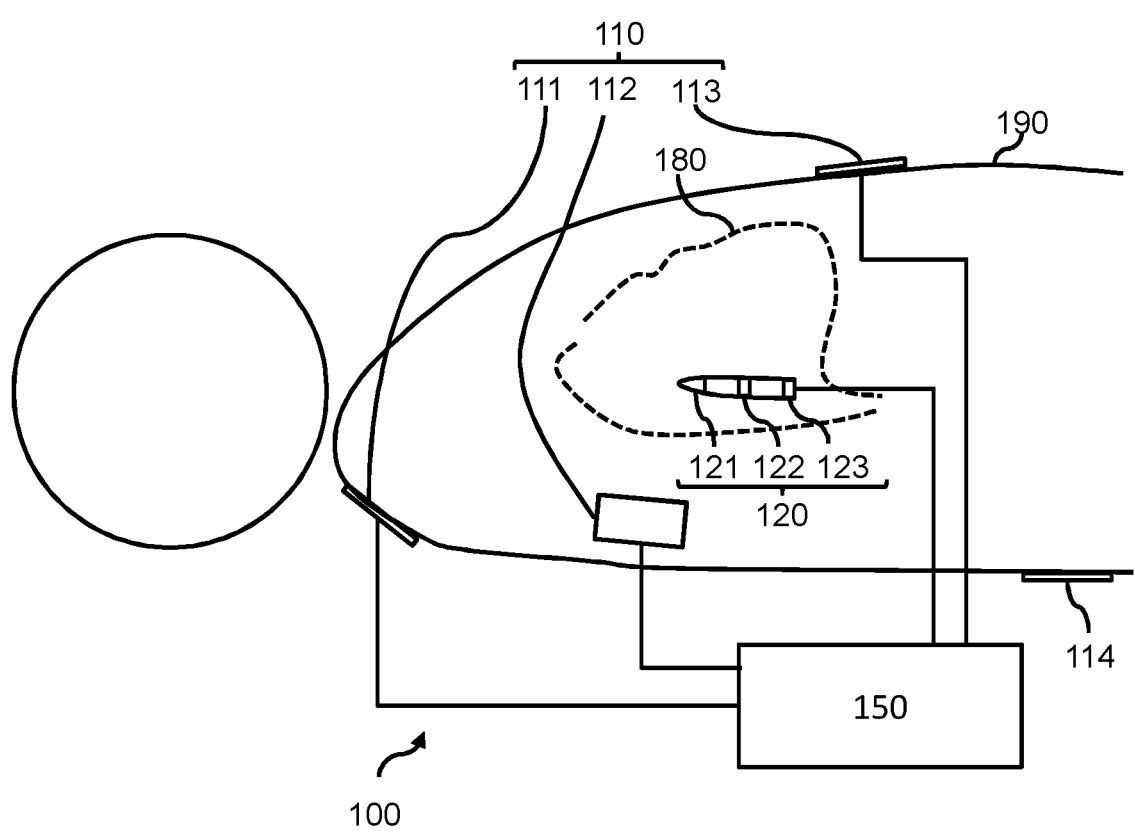
FIG. 1 illustrates a dielectric imaging system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a mechanism for registering ultrasound images with an anatomical map generated using a dielectric imaging process. The positions of electrodes that move with the ultrasound probe are monitored using the same dielectric imaging system that generated the anatomical map. The position at which ultrasound images are generated is captured, and this information is used to register the ultrasound image(s) with respect to the anatomical map.

Embodiments are based on the realization that a same dielectric imaging system that tracks the position of electrodes to generate an anatomical map can be used to track electrodes on an ultrasound probe to register any generated ultrasound images with respect to the anatomical map. In other words, the relative spatial position between an ultrasound image and the anatomical map can be derived by identifying the location of the ultrasound probe as it takes the ultrasound image.

Concepts of the invention can be employed in any suitable medical environment in which internal, such as intravascular (and preferably intracardiac), ultrasound imaging is desired.

FIG. 1 illustrates a dielectric imaging system 100 for generating an anatomical model (of a volume or interest, i.e. an anatomical cavity, such as a blood vessel, heart (chamber), stomach or lung(s)) using a dielectric imaging process.

The dielectric imaging system 100 builds an anatomical model of a volume of interest 180 (e.g. a chamber, vessel or void) within a subject 190 by measuring the influence of tissue surrounding the volume of interest on an electric field generated by a plurality of electrodes. This allows the boundaries, border or perimeter of a volume of interest to be mapped, thereby building an anatomical model of the volume of interest.

The dielectric imaging system 100 comprises a first set 110 of electrodes, 111, 112, 113 ("external electrodes") to be positioned externally with respect to the subject 190 (e.g. patch electrodes provided on a skin of the subject). The first set 110 of electrodes may comprise a plurality of electrodes angled with respect to one another (e.g. positioned orthogonally to one another), so that any electric fields generated by the electrodes are angled with respect to one another. The first set 110 of electrodes may also comprise a reference electrode 114. It is noted that there may be more than the illustrated number of external electrode.

The dielectric imaging system 100 also comprises a second set 120 of electrodes 121, 122, 123 ("internal electrodes") to be positioned within the volume of interest (e.g. electrodes positioned on a catheter 125 or other intravascular device to be inserted into the volume of interest). A distance between each of the second set of electrodes may be predetermined and/or known. At least two electrodes are required for high quality tracking of the position of the catheter or other intravascular device.

A dielectric imaging processor 150 is configured to provide and receive signals from the electrodes 110, 120 to perform a dielectric imaging process. The dielectric imaging processor 150 builds up an anatomical model of the volume of interest (e.g. as the catheter 125 moves through the volume of interest), and can track a relative location of the internal electrodes 120 with respect to the volume of interest 180.

The dielectric imaging system 100 operates by generating a global intra-body electrical field using the external electrodes, optionally together with a local electrical field via the internal electrodes. The external electrodes (and internal electrodes, if used to generate the local electrical field) are all both emitters and receivers of an electric field, which may be in the frequency range of 10-100 kHz (although other larger/smaller ranges are contemplated). The reference electrode serves as an electric reference for all voltage measurements.

The induced electrical fields' distribution is inherently inhomogeneous due to the different dielectric properties and absorption rates (related to conductivity) of the interrogated tissues. The external electrodes act to measure the global general effects and distorted electrical field whereas the internal electrodes measure the local effect and tissue response.

The dielectric imaging processor 150 may control the external electrodes to generate electrical fields of different frequencies (and in different directions). This results in an internal electrode having a different response to the externally applied electric fields based on its relative position within the volume of interest.

For instance, if there are three external electrodes 111, 112, 113 positioned to emit electric fields of different frequencies ($E_1$, $E_2$, $E_3$) that are angled (e.g. near-orthogonal) with respect to one another, a voltage response ($V_1$, $V_2$, $V_3$) of an internal electrode (identifying a voltage (e.g. between the electrode and the reference electrode or between the electrode and the electrode generating the electric field) at each of these three frequencies) will differ depending upon position within the volume of interest. Other forms of response (e.g. an impedance response or a capacitive, e.g. indicating change in impedance/capacitance between the internal electrode and each external electrode) will be apparent to the skilled person.

Throughout an imaging process, the response of the internal electrodes (e.g. to externally applied electric fields) is recorded. The dielectric imaging processor applies a transfer function ("V2R function") that transforms each recorded electrical response (e.g. voltages) to Euclidian coordinates (R-space), whilst ensuring known catheter properties (e.g. electrode spacing) as well as a set of other constraints are maintained.

In this way, an R-space cloud of points (having known Euclidian co-ordinates) can be built up and updated as the internal electrodes are moved within the volume of interest. Using the R-space cloud of points, a reconstruction algorithm generates an anatomical model of the volume of interest. The anatomical model may, for example, be a 3D surface that depicts or models the (bounds of) the volume of interest.

The anatomical model may be output to a display or user interface (not shown).

Figure 2:
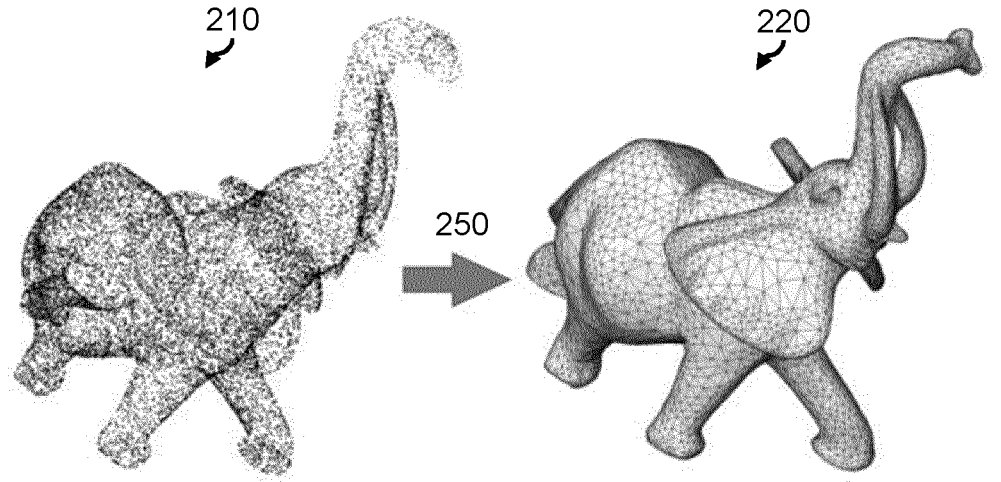
FIG. 2 demonstrates a process for generating an anatomical map.

The process of reconstructing an anatomical model from a point cloud is conceptually illustrated in FIG. 2, which demonstrates a process 250 in which a cloud of R-space points 210 ("point cloud") is transformed into an anatomical model 220. In the illustrated example, this is performed by creating a (3D) surface from the point cloud data, methods of which will be readily apparent to the skilled person.

For example, a point cloud can be converted into a polygon mesh or triangular mesh model (or other surface model) using a surface reconstruction approach. A variety of suitable approaches is discussed in Berger, Matthew, et al. "A survey of surface reconstruction from point clouds." Computer Graphics Forum. Vol. 36. No. 1. 2017.

In this way, the "global field" measurements (i.e. the effect of the external electrodes on the internal electrodes) can be used to generate a rough anatomical model of the volume of interest.

More precise identification of the bounds and features of the anatomical model can be performed by monitoring the response of the internal electrodes to local field measurements (e.g. fields generated by other internal electrodes) or through additional processing of global field measurements.

The combined global and local field measurements enable sophisticated detection and effective handling of inconsistencies and outliers, level of electrode shielding/coverage (e.g. by measuring location inter-correlation), pacing (saturation), as well as physiological drift. Drift can, for example, be detected using a moving window over time and corrected continuously whereby the catheter location remains accurate throughout the whole procedure making the system resilient to drift.

The above-provided description of a dielectric imaging system is only an example, and the skilled person would be readily capable of modifying the described dielectric imaging system appropriately. For example, other types of electrical response could be monitored to monitor a location of electrode(s) and/or to generate the anatomical map.

The present disclosure exploits the presence and operation of a dielectric imaging system to facilitate registering of (internally obtained) ultrasound images to an anatomical map generated using the dielectric imaging system. In other words, the present disclosure proposes a mechanism for enabling the anatomical map and the ultrasound images to share a same co-ordinate system, i.e. aligning the ultrasound images and the anatomical map with respect to one another. Put yet another way, the spatial relationship between the anatomical map and the one or more ultrasound images can be determined.

Embodiments of the present disclosure propose to exploit the operation of the dielectric imaging system to track a location of electrodes that move with an ultrasound imaging probe with respect to the anatomical model, i.e. to act as an electrode tracking system.

It will be apparent that, once an anatomical model of a volume of interest has been constructed using responses of internal electrodes within the volume of interest, then the location of internal electrodes with respect to the anatomical model can be readily defined. For example, the transfer function (which transforms a response to Euclidian coordinates) can be used to calculate/predict a relative position of any other internal electrode using the response of the internal electrode.

In this way, a response of an electrode to an electric field may be used to identify a relative location of that electrode with respect to the anatomical map. This can be performed by transforming a response of an electrode to an electric field to a co-ordinate using the "V2R function".

The present disclosure proposes to provide an ultrasound imaging system with two or more electrodes that move as an ultrasound imaging probe is moved within a volume of interest (having an anatomical map) of the patient. The dielectric imaging system can then be used to track a relative location of the ultrasound imaging probe within the volume of interest (in a similar manner as to how the relative location of internal electrodes of the dielectric imaging system are tracked). In other words, the relative position of the electrode(s) of the ultrasound imaging system are tracked in the same 3D space as the electrodes used to generate the anatomical map. This facilitates (spatial) registration of an ultrasound image generated by the ultrasound probe to the anatomical map.

It is recognized that once the position (and preferably orientation/angle) of an ultrasound probe (when taking an ultrasound image) with respect to an anatomical map is known, then the ultrasound images generated by the ultrasound probe can be accurately mapped or registered with respect the anatomical map. In particular, the position of the source of the ultrasound image (i.e. the position of the points at which the ultrasound image is taken) can be monitored and used to spatially register the ultrasound image with respect to the anatomical map.

By its nature, the positional relationship between an area represented by an ultrasound image and the ultrasound probe is known. That is, a direction and origin of a field of view or "viewing cone" provided by an ultrasound image will be dependent upon the position of the ultrasound probe when taking the ultrasound image. Thus, by determining a position of the ultrasound probe with respect to an anatomical map, a positional relationship between ultrasound image and an anatomical map can also be determined. This means that an ultrasound image providing a representation of a particular anatomical area can be matched to part of the anatomical map representing the same anatomical area.

Optionally, the orientation of the ultrasound probe within the volume of interest can also be determined, in order to improve the registration of the ultrasound image(s), generated using the ultrasound probe, with the anatomical map, e.g. to facilitate accurate overlaying of the ultrasound image(s) over the anatomical map.

The orientation of the ultrasound probe defines the position/angle of the longitudinal axis of the ultrasound probe within the 3D space of the anatomical map. This is to be distinguished from a "rotation" or "roll" of the ultrasound probe, which defines the rotation of the ultrasound probe about its longitudinal axis, thereby defining an imaging direction from the longitudinal axis of the ultrasound probe.

By determining the orientation of the ultrasound probe, when taking the ultrasound image, the angle of the ultrasound image with respect to the anatomical map can also be determined. A similar understanding will be apparent using the roll of the ultrasound probe.

Figure 3:
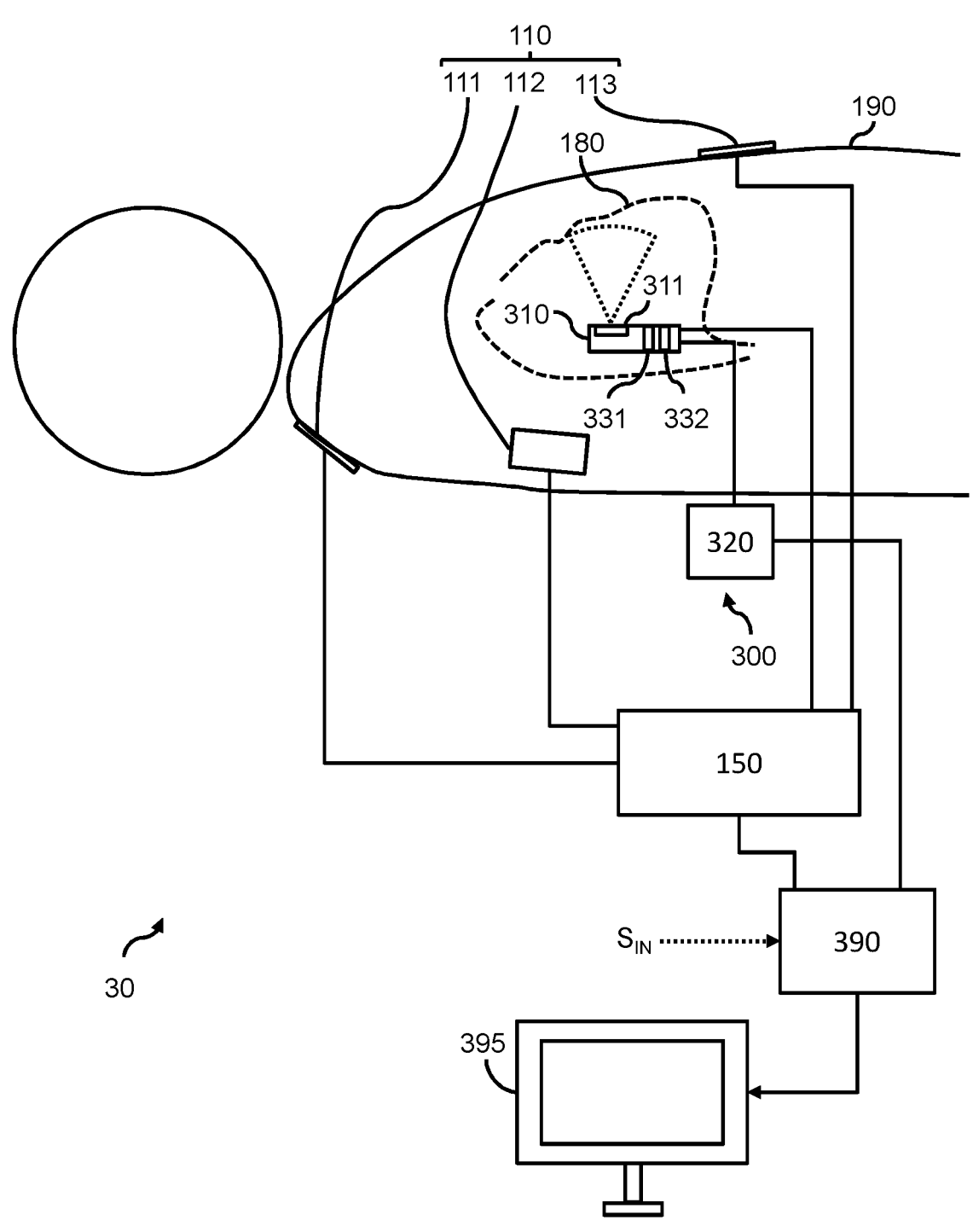
FIG. 3 illustrates an ultrasound system.

FIG. 3 illustrates an ultrasound image system 300 for use in an example embodiment. The ultrasound image system may form part of an overall imaging system 30.

The ultrasound system 300 comprises an ultrasound probe 310 configured to obtain ultrasound data, e.g. using an ultrasound array 311.

The ultrasound probe may comprise any suitable ultrasound probe designed for performing internal ultrasound imaging of a volume of interest of a patient. Thus, the ultrasound probe may an intravascular (IV) ultrasound probe, such as an intracardiac echographic (ICE) catheter probe, an endoscopic ultrasound probe, transrectal ultrasound probe or the like.

The ultrasound probe 310 may be configured to generate ultrasound pulses and receive ultrasound echoes, and generate ultrasound data responsive to the ultrasound echoes. The operating procedure of an ultrasound probe is well known in the art.

The ultrasound system 300 also comprises an ultrasound processing module 320. The ultrasound process module is configured to generate at least one ultrasound image of the volume of interest by processing the ultrasound data provided by the ultrasound probe 310. For example, the ultrasound data can be used to generate one or more ultrasound images (e.g. a 2D/3D ultrasound image, an ultrasound video and/or mixed-media data, such as a Doppler flow).

The ultrasound system 300 also comprises two or more electrodes 331, 332, connectable to the dielectric imaging system, and configured to move together with a movement of the ultrasound probe. The spatial relationship between the electrodes and the ultrasound probe may be known or predetermined. Each electrode may be positioned at a different position with respect to a longitudinal axis of the ultrasound probe 300.

Thus, the dielectric imaging system 150 may be capable of monitoring and/or controlling electrical signals from/at the electrodes.

The electrodes facilitate tracking of the relative position or "localization" of the (tip of the) ultrasound probe within the volume of interest, e.g. relative to the location of any external electrodes of the dielectric imaging system, using the dielectric imaging system. Thus, the dielectric system can monitor the position of the ultrasound probe within the volume of interest.

A registration module 390 can be configured to register a position of each at least one ultrasound image with respect to the anatomical map of the volume of interest using the monitored positions of the ultrasound probe. Thus, the registration module may place the anatomical map and the one or more ultrasound image(s) in a same co-ordinate system.

This is achievable because a same system is used to track the position of the ultrasound probe as is used to track the internal electrodes used when generating the anatomical map. Thus, the movement/position of the ultrasound probe can be localized with respect to the anatomical map, meaning that the position of each ultrasound image (i.e. the position at which the ultrasound probe is located when it obtains the ultrasound data used to generate the ultrasound image) can be obtained and mapped to the corresponding position with respect to the anatomical map.

Moreover, the use of two or more electrodes for the ultrasound probe facilitates determination of the position of the longitudinal axis of the ultrasound probe, i.e. the orientation of the ultrasound probe. In particular, if the location of each of the electrodes of the ultrasound probe with respect to the anatomical model is known, and a spatial relationship between the electrodes is known, then the position of the longitudinal axis of the ultrasound probe with respect to the anatomical model can be tracked. This is because the electrodes define the position (with respect to the anatomical map) at least two points of the longitudinal axis, allowing the longitudinal axis (and therefore a range of possible imaging directions) of the ultrasound probe to be determined.

This facilitates increased ease in registering any ultrasound images generated using the ultrasound probe with the anatomical map.

This means that information on the imaging direction can be obtained through the use of two or more electrodes, i.e. information on how the ultrasound image relates to the anatomical map. Hence no other position sensors need be used. In particular magnetic positions sensors need not be used. A magnetic position sensor typically comprises three non-concentric coils (not shown), such as described in U.S. Pat. No. 6,690,963. Other such magnetic position sensors comprising any number of concentric or non-concentric coils, Hall-effect sensors or magneto-resistive sensors.

The electrodes 331, 332 may be mounted directly on the ultrasound probe 310 (as illustrated). In some examples, the electrodes may comprise dedicated electrodes, such as ring electrodes or partial ring electrodes.

It is recognized that ultrasound probes can comprise one or more existing metal structures, e.g. to support, protect or reinforce other elements of the ultrasound probe (such as a metal stiffener for protecting an ultrasound array). In some examples, one or more of any existing metal structures may be repurposed to further act as an electrode (e.g. by connecting the existing metal structure to a wire).

In other examples, the two or more electrodes 331, 332 may be mounted so that they move together with a movement of the ultrasound probe, but are not directly mounted thereon. For example, the ultrasound probe may comprise a catheter, which is mounted in a sheath upon which the electrodes are mounted. Positioning electrodes on a sheath means that different types of ultrasound probes (e.g. updated versions) could be used with the same type of sheath, whilst still retaining the ability to monitor a relative position of the ultrasound probe with respect to the external electrodes of the dielectric imaging system.

Other examples will be apparent to the skilled person.

Registering the position of at least one ultrasound image with respect to the anatomical map of the volume of interest enables a display (e.g. a screen) to provide a visual representation of the anatomical map and the at least one ultrasound image that are registered together.

In other words, a visual representation of the anatomical map produced by the dielectric imaging system can be augmented by showing one or more ultrasound images on/overlaying the anatomical map. The one or more ultrasound images may comprise, for example, 2D/3D, X-plane or Doppler ultrasound images.

The display may be controlled in real time, e.g. to display a most recently acquired ultrasound image overlaid upon an anatomical map of the volume of interest, derived by dielectric imaging.

In some examples, the imaging system 30 may further comprise a display 395 configured to display the anatomical map generated by the dielectric imaging system; and one or more ultrasound images obtained by the ultrasound imaging system, wherein the one or more ultrasound images overlay the anatomical map based on at least the registered position of each one or more ultrasound image with respect to the anatomical map.

It will be apparent that the imaging direction or field of view of the ultrasound probe (i.e. the direction or directions from which ultrasound data is obtained) may also be dependent upon the orientation or "roll" of the ultrasound probe. In particular, if the ultrasound probe rotates about its longitudinal axis (roll) within the volume of interest, the ultrasound data may be obtained from different directions from the longitudinal axis of the ultrasound probe with respect to the volume of interest.

It may be beneficial to determine the imaging direction of the ultrasound probe with respect to the anatomical map. This enables ultrasound images of the volume of interest to be correctly oriented/positioned with respect to the anatomical map (e.g. in a display), to improve a clinician's understanding of the area of the volume of interest being imaged.

In some examples, the registration module 390 may be configured to register the anatomical map and the one or more ultrasound images together further based on the determined roll of the ultrasound probe.

Various mechanisms for determining the relative roll of the ultrasound probe with respect to the anatomical map are envisaged.

In one example, the ultrasound imaging system 300 further comprises an accelerometer configured to monitor a roll and optionally orientation of the ultrasound probe, with respect to the volume of interest, during the ultrasound imaging process. The imaging system can thereby be configured to determine an imaging direction of each at least one ultrasound image based on the monitored orientation of the ultrasound probe during the ultrasound imaging process.

In another example, the registration module 390 may be configured to perform, for at least one ultrasound image, an image feature matching process on the ultrasound image and the anatomical map to thereby identify a roll of the ultrasound probe or imaging direction of each at least one ultrasound image with respect to the anatomical map.

In other words, the registration module may identify features (e.g. anatomical landmarks) present in both the ultrasound image(s) and the anatomical map, and determine an imaging direction of the ultrasound probe based on the presence of similar/same image features in both the ultrasound image(s) and the anatomical map. By way of example only, where the volume of interest is a chamber of the heart, the identified features may include landmarks such as the pulmonary vein(s), left atrial appendage, or mitral valve.

Methods for identifying similar image features in both the anatomical map and the ultrasound image(s) will be apparent to the skilled person, e.g. employing an image recognition process and/or machine-learning approaches to recognize similar features.

In yet another example, the registration module 390 may be configured to receive a user input $S_{IN}$ that indicates, for at least one ultrasound image, a roll of the ultrasound probe with respect to the anatomical map. This may allow, for example, a clinician to use their expertise to indicate an imaging direction for an ultrasound image, to facilitate ease of overlaying an ultrasound image over an anatomical map.

In yet another example, an integrated optical shape sensed fiber can be added to the ultrasound probe to measure in real time the 3D shape and position of the ultrasound probe.

In particular, the ultrasound system 300 may further comprise an optical fiber that moves together with a movement of the ultrasound probe 310. An optical shape determination module (of the imaging system) may be configured to transmit and receive electromagnetic radiation along the optical fiber of the ultrasound system to monitor a shape of the optical fiber, and thereby a position, orientation and/or roll of (both the) the optical fiber and the ultrasound probe.

This approach facilitates the registration of the ultrasound image(s) with the anatomical map. Using optical shape sensing techniques is known to provide highly accurately information on the relative position, orientation and/or roll of a catheter or other probe within a cavity, void, vessel or chamber of a patient.

Moreover, the intrinsic 3D localization accuracy of the optical shape sensed fiber can also provide a reference to improve the electrode localization accuracy of the dielectric imaging system, which may be sensitive to non-linearities of electric fields (e.g. such as those caused by the human thorax).

In other words, where the ultrasound probe comprises an integrated optical shape sensed fiber, the determined location of the ultrasound probe can be used to increase an accuracy of electrode localization performed by the dielectric imaging system. This can, for example, cause the dielectric imaging system to modify the anatomical map based on the highly accurate electrode localization performed by the optical shape sensed fiber.

Furthermore, the patient specific 3D shape of the vasculature system in which the ultrasound probe is positioned makes registration of the ultrasound images and/or anatomical to pre-recorded medical images (e.g. CT images) or recordings possible. For example, the patient specific space and length of the vascular pathway to a volume of interest can be visualized. The ultrasound probe will be placed inside this characteristic vascular shape/length, hence a registration between pre-recorded CT and intra-procedural obtained shape and 3D anatomical map can be made.

In other words, ultrasound image(s) and/or the anatomical map can be registered with other medical images through use of the optical shape sensed fiber (as this can track the shape of a user's blood vessels, which can be identified in pre-existing medical images to aid in registration of the images/map).

Other examples for detecting a roll of the ultrasound probe may use appropriately configured electrodes to exploit the operation of the dielectric imaging system to determine the roll (and imaging direction) of the ultrasound probe.

In particular, the electrode(s) may be configured to have non-infinite rotational symmetry, i.e. be non-circular, non annular or the like. In other words, the electrodes may not span an entire circumference of the ultrasound probe but rather may cover only a section of the circumference. In this way, the response(s) of the electrodes to electric fields induced by the dielectric imaging system (e.g. by the external electrodes of the dielectric imaging system) differ depending upon the roll of the ultrasound probe. In this way, it can be a priori known how the configuration correlates with the imaging direction of the ultrasound imaging array (i.e. the roll of the ultrasound probe).

In some examples, different electrodes may be exposed to different sides of the ultrasound probe (or a connected element). In this way, a difference between the response of each electrode to an electric field (e.g. induced by an external electrode of the dielectric imaging system) can be used to determine a relative rotation/roll of the ultrasound probe within the volume of interest.

Figures 4, 5:
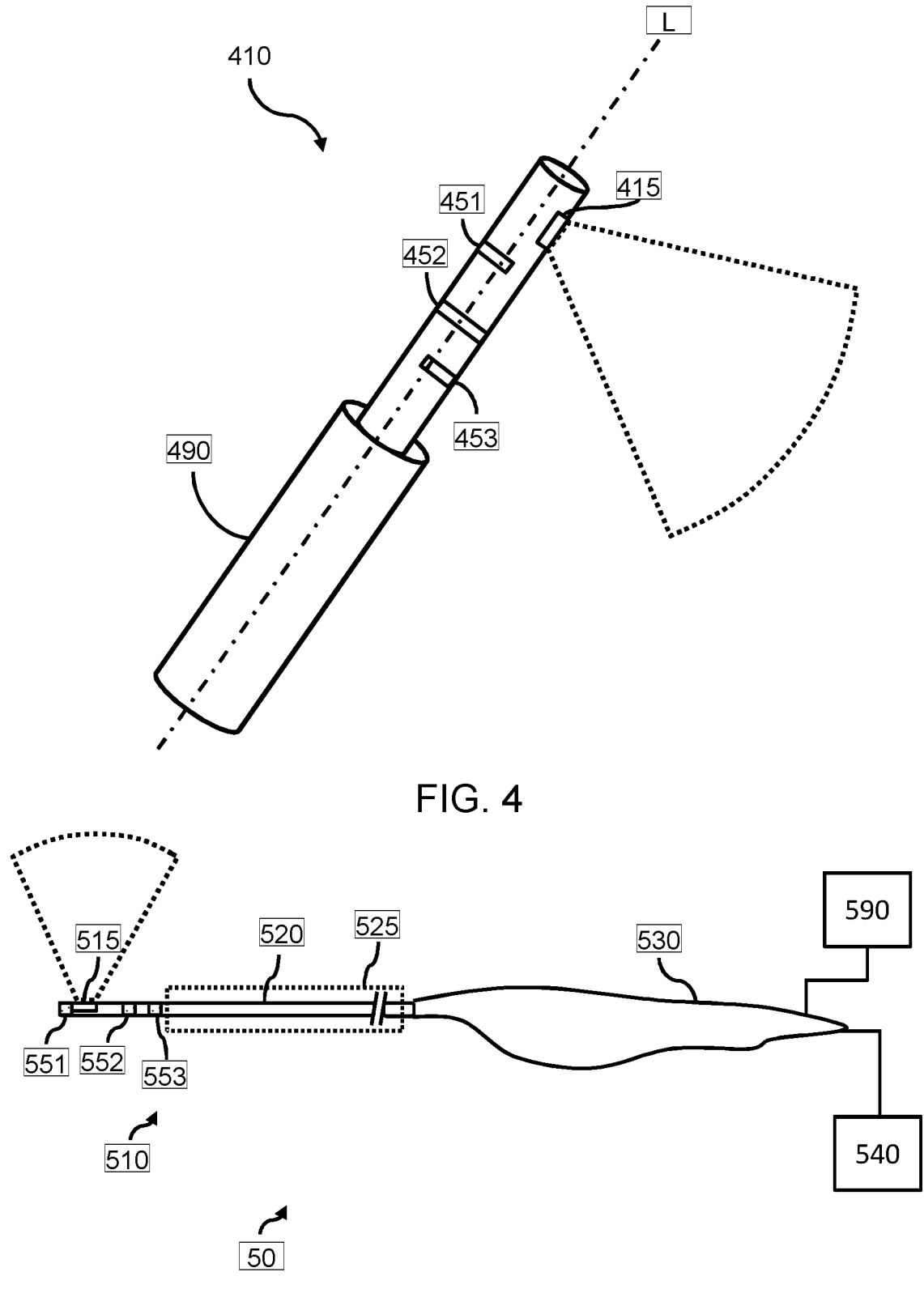
FIG. 4 illustrates an ultrasound probe.
FIG. 5 illustrates another ultrasound system.

FIG. 4 illustrates a portion of an ultrasound probe 410. The ultrasound probe 410 is an example of the ultrasound probe 310 illustrated in FIG. 3.

The ultrasound probe 410 comprises an ultrasound array 415 for capturing ultrasound data.

The electrodes 451-453 of the ultrasound imaging system are here illustrated as being mounted upon the ultrasound probe. However, they may be mounted on other elements that move together with the ultrasound probe (e.g. a sheath 490). This can facilitate the use of standard or "off-the-shelf" ultrasound probes with the ultrasound imaging system.

The electrodes 451-453 are configured to have non-infinite rotational symmetry, and are also positioned so as to be exposed to different sides of the ultrasound probe. This facilitates, as previously explained, determination of the rotation (i.e. the "roll") of the ultrasound probe.

In other examples, the electrodes may be ring electrodes (e.g. rotationally symmetric), but one or more portions of the electrodes may be shielded (e.g. using an appropriately configured sheath or the like), to have the same effect as providing electrodes of non-infinite rotational symmetry.

FIG. 5 illustrates an ultrasound imaging system 50 for use in an example embodiment.

The ultrasound imaging system 50 comprises an ultrasound probe 510, which is configured to obtain ultrasound data about a volume of interest during an ultrasound imaging process. This ultrasound data is processed by an ultrasound processing module 540, to obtain one or more ultrasound images during an ultrasound imaging process.

The ultrasound probe 510 comprises a transducer array 515 controllable to transmit ultrasound pulses and receive echoes of the transmitted ultrasound pulses to thereby generate the ultrasound data. The transducer array is mounted upon a catheter 520 that can be inserted through a vessel/duct of a patient (e.g. a vein) to reach a volume of interest.

The catheter 520 may pass through a sheath 525, which can protect sensitive components (such as the transducer 515) of the ultrasound probe during transit to the volume of interest, before they are exposed.

The ultrasound probe further comprises a handle 530, which can be held by a clinician during insertion of the catheter into the patient, to move the ultrasound array 515 to the volume of interest. Control elements may be mounted upon the handle One or more wires for transmitting ultrasound data from the transducer array may span the length of the catheter 520 (e.g. to terminate in the handle 530). In particular, the wires may be electrically connectable to an ultrasound processing module 540, which is capable of obtaining the ultrasound data and processing it to generate one or more ultrasound images. Of course, the ultrasound processing module 540 may similarly control the operation of the ultrasound array 515, as would be well known to the skilled person.

The ultrasound imaging system 50 also comprise a plurality of electrodes 551-553, which are here mounted on the ultrasound probe 510 (in particular, the catheter 520). In other examples, they are mounted on the sheath 525 or another accompanying components.

The operation and/or monitoring of these electrodes 551-553 is performed by a dielectric imaging system (rather than the ultrasound processing module 540).

Wires for monitoring and/or a controlling an electric field at the plurality of electrodes may also span the length of the catheter 520. The wires may be electrically connectable to the dielectric imaging system, to facilitate monitoring of the position of the ultrasound probe (and therefore enable registration of ultrasound images to an anatomical map generated by the dielectric imaging system).

Figure 6:
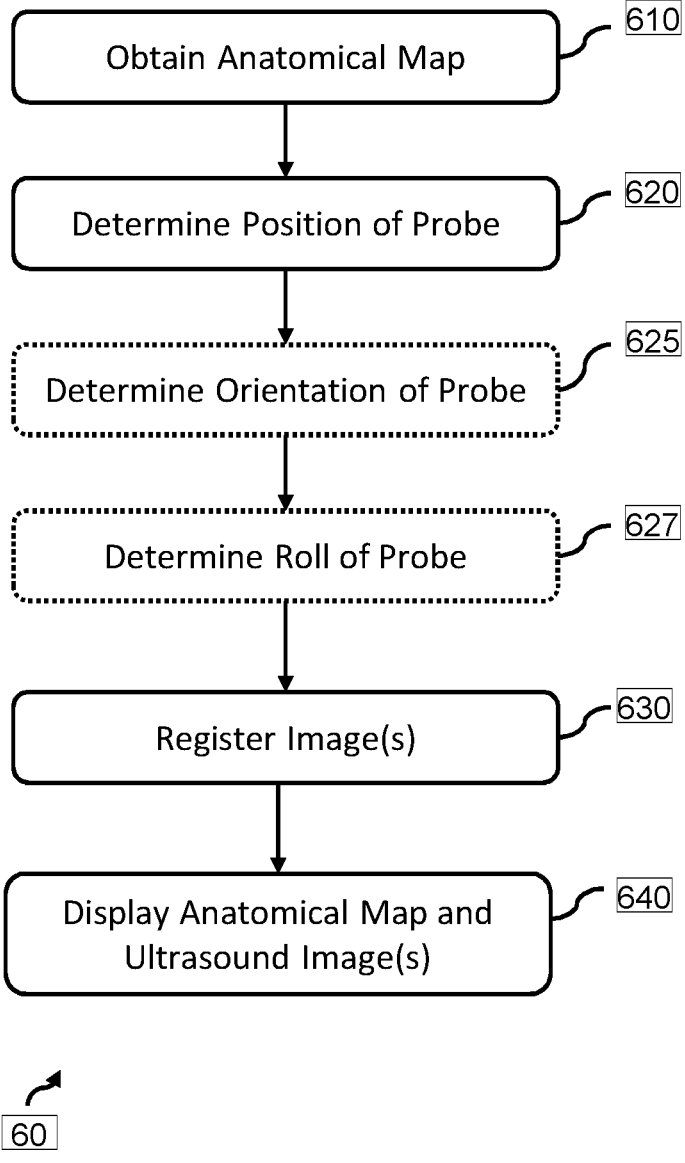
FIG. 6 illustrates a method.

FIG. 6 illustrates a method 60 for registering at least one ultrasound image obtained using an ultrasound probe during an ultrasound imaging process to an anatomical map. The method 60 may be performed by the registration module previously described.

The method comprises a step 610 of obtaining an anatomical map of a volume of a subject generated using a dielectric imaging system configured to use dielectric imaging to obtain an anatomical map. The anatomical map may be obtained, for example, from a separate dielectric imaging system.

The method 60 comprises a step 620 of monitoring/determining a position of the probe, with respect to the anatomical map, during the ultrasound imaging process. Suitable methods for this process have previously been described.

The method 60 may comprise a step 625 of determining an orientation of the probe, and specifically an orientation of a longitudinal axis of the ultrasound probe. The method may also comprise a step 627 of determining a roll of the ultrasound probe, e.g. a rotation of the probe about the longitudinal axis. Suitable approaches for carrying out steps 625 and 627 have been previously described.

The method 60 further comprises a step 630 using the monitored/determined position(s) of the ultrasound probe to register at least one ultrasound image to the anatomical map.

Step 630 may comprise determining a relative position of the ultrasound image with respect to the anatomical map using the determined position of the probe when taking the ultrasound image. Step 630 may orient the ultrasound image with respect to the anatomical map by using the determined orientation of the probe when taking said ultrasound image. Step 630 may further orient or position the ultrasound image with respect to the anatomical map using the determined roll of the ultrasound.

The method 60 may further comprise a step 640 of displaying the anatomical map and the registered ultrasound image at a visual display. Step 640 may comprise displaying the anatomical map with the registered ultrasound image overlaying the anatomical map at the determined position and/or orientation of the ultrasound image.

As another example, step 640 may comprise displaying the anatomical map and an indication of the viewing direction (e.g. identifying an origin and direction) at which the ultrasound image was taken. This may give a visual indication of the area of the volume of interest imaged by the ultrasound image. A separate display of the ultrasound image may also be provided.

Step 640 may further comprise displaying a visual representation of the ultrasound probe with respect to the anatomical map, e.g. based on the position of the probe as determined in step 620 and optionally the orientation of the probe as determined in step 625.

The anatomical map generated by the dielectric imaging system may be generated using the electrical response(s) of electrodes mounted to move with the ultrasound probe (i.e. electrodes of the ultrasound system). In other examples, the anatomical map generated by the dielectric imaging system may be generated using the electrical response(s) of electrodes mounted on another catheter (e.g. another intravascular device used before use of the ultrasound probe). In yet other examples, the electrical response(s) from both types of electrode can be used.

It will be understood that disclosed methods are preferably computer-implemented methods. As such, there is also proposed the concept of a computer program comprising computer program code for implementing any described method when said program is run on a processing system, such as a computer or a set of distributed processors.

Different portions, lines or blocks of code of a computer program according to an embodiment may be executed by a processing system or computer to perform any herein described method. In some alternative implementations, the functions noted in the block diagram(s) or flow chart(s) may occur out of the order noted in the Figures. For example, two blocks shown in succession may, in fact, be executed substantially concurrently, or the blocks may sometimes be executed in the reverse order, depending upon the functionality involved.

The present disclosure proposes a computer program (product) comprising instructions which, when the program is executed by a computer or processing system, cause the computer or processing system to carry out (the steps of) any herein described method. The computer program (product) may be stored on a non-transitory computer readable medium.

Similarly, there is also proposed a computer-readable (storage) medium comprising instructions which, when executed by a computer or processing system, cause the computer or processing system to carry out (the steps of) any herein described method. There is also proposed computer-readable data carrier having stored thereon the computer program (product) previously described. There is also proposed a data carrier signal carrying the computer program (product) previously described.

The computer-readable program may execute entirely on a single computer/processor, partly on the computer/processor, as a stand-alone software package, partly on the computer/processor and partly on a remote computer or entirely on the remote computer or server (e.g. using a distributed processor processing system). In the latter scenario, the remote computer may be connected to the computer/processor through any type of network, including a local area network (LAN) or a wide area network (WAN), or the connection may be made to an external computer (for example, through the Internet using an Internet Service Provider).

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims.

The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to".

Any reference signs in the claims should not be construed as limiting the scope.

The invention claimed is:

1. A system for registering at least one ultrasound image obtained using an ultrasound probe during an ultrasound imaging process to an anatomical map obtained using a dielectric imaging process, the system comprising:
   a dielectric imaging system configured to generate an anatomical map of a volume of interest of a subject using a dielectric imaging process;
   an ultrasound imaging system configured to generate one or more ultrasound images of the volume of interest, the ultrasound imaging system comprising:
      an ultrasound probe configured to obtain ultrasound data of the volume of interest during an ultrasound imaging process;
      an ultrasound processing module configured to process the ultrasound data, obtained during the ultrasound imaging process, to generate at least one ultrasound image of the volume of interest; and
      two or more electrodes, connectable to the dielectric imaging system, and configured to move together with a movement of the ultrasound probe;
   wherein the dielectric imaging system is further configured to connect to the two or more electrodes of the ultrasound imaging system and monitor positions of the two or more electrodes, and thereby the ultrasound probe, during the ultrasound imaging process;
   a registration module configured to register a position of each at least one ultrasound image with respect to the anatomical map of the volume of interest using the monitored positions of the ultrasound probe.

2. The imaging system of claim 1, wherein the dielectric imaging system is configured to monitor positions of the two or more electrodes by monitoring an electrical response of each electrode to one or more electric fields induced in the subject.

3. The imaging system of claim 1, wherein:
   the ultrasound imaging system, the dielectric imaging system and/or the registration module is configured to determine an imaging direction of each at least one ultrasound image; and
   the registration module is configured to register an orientation of each at least one ultrasound image with respect to the anatomical map of the volume of interest based on the determined imaging direction of each at least one ultrasound image.

4. The imaging system of claim 3, wherein:
   the ultrasound imaging probe further comprises an accelerometer configured to monitor an orientation of the ultrasound probe, with respect to the volume of interest, during the ultrasound imaging process; and
   the imaging system is configured to determine an imaging direction of each at least one ultrasound image based on the monitored orientation of the ultrasound probe during the ultrasound imaging process.

5. The imaging system of claim 3, wherein:
   the registration module is configured to perform, for at least one ultrasound image, an image feature matching process on the ultrasound image and the anatomical map to thereby identify an imaging direction of each at least one ultrasound image with respect to the anatomical map.

6. The imaging system of claim 3, wherein the registration module is configured to receive a user input indicating, for at least one ultrasound image, an orientation of the at least one ultrasound image with respect to the anatomical map.

7. The imaging system of claim 3, wherein the two or more electrodes of the ultrasound imaging system comprise two or more non-cylindrical electrodes positioned along a longitudinal axis of the ultrasound probe,
   wherein the dielectric imaging system is configured to determine an orientation of the two or more electrodes, and therefore the ultrasound probe, by monitoring electric fields and therefore the 3D positions by the non-cylindrical electrodes.

8. The imaging system of claim 1, wherein at least one of the electrodes of the ultrasound system is used as a support structure for one or more elements of the ultrasound probe.

9. The imaging system of claim 1, wherein:
   the ultrasound system further comprises an optical fiber that moves together with a movement of the ultrasound probe,
   the imaging system further comprises an optical shape determination module configured to transmit and receive electromagnetic radiation along the optical fiber of the ultrasound system to monitor a shape of the optical fiber, and thereby a position and/or orientation of the optical fiber and the ultrasound probe.

10. The imaging system of claim 9, wherein:
   the imaging system further comprises a three-dimensional medical image obtainer, configured to obtain a three-dimensional medical image of the patient, containing at least the volume of interest; and
   the registration module is configured to use the monitored shape of the optical fiber to further register the position of the at least one ultrasound image, and optionally the anatomical map, with respect to the three-dimensional medical image.

11. The imaging system of claim 1, wherein the at least two electrodes are disposed in or on a sheath that houses the ultrasound probe.

12. The imaging system of claim 1, wherein the dielectric imaging system is configured to generate the anatomical map of the volume of interest by performing a dielectric imaging process using the two or more electrodes of the ultrasound imaging probe.

13. The imaging system of claim 1, further comprising a display configured to display:

the anatomical map generated by the dielectric imaging system; and one or more ultrasound images obtained by the ultrasound imaging system, wherein the one or more ultrasound images overlay the anatomical map based on at least the registered position of each one or more ultrasound image with respect to the anatomical map.

14. A computer-implemented method for registering at least one ultrasound image obtained using an ultrasound probe during an ultrasound imaging process to an anatomical map, the computer-implemented method comprising:

obtaining an anatomical map of a volume of a subject generated using a dielectric imaging system configured to use dielectric imaging to obtain an anatomical map;

monitor, during the ultrasound imaging process, positions of the ultrasound probe with respect to the subject using the dielectric imaging system, wherein the ultrasound probe comprises two or more electrodes detectable by the dielectric imaging system; and using the monitored positions of the ultrasound probe to register at least one ultrasound image generated using the ultrasound probe with a respective position in the anatomical map, to thereby register at least one ultrasound image to the anatomical map.

15. A computer system configured to register at least one ultrasound image obtained using an ultrasound probe during an ultrasound imaging process to an anatomical map comprising:

a processor configured by one or more machine-readable instructions to:

obtain an anatomical map of a volume of a subject generated using a dielectric imaging system configured to use dielectric imaging to obtain an anatomical map;

monitor, during the ultrasound imaging process, positions of the ultrasound probe with respect to the subject using the dielectric imaging system, wherein the ultrasound probe comprises two or more electrodes detectable by the dielectric imaging system; and register, using the monitored positions of the ultrasound probe, at least one ultrasound image generated using the ultrasound probe with a respective position in the anatomical map, to thereby register at least one ultrasound image to the anatomical map.

\* \* \* \* \*